United States Patent [19]

Reinhoudt et al.

[11] Patent Number: 4,735,702
[45] Date of Patent: Apr. 5, 1988

[54] METHOD OF PRODUCING AN ISFET AND SAME ISFET

[75] Inventors: David N. Reinhoudt, Hengelo; Marcel L. M. Pennings, Horst; Auke G. Talma, Hengelo, all of Netherlands

[73] Assignee: Stichting Centrum Voor Micro-Electronica Twente, Enschede, Netherlands

[21] Appl. No.: 807,508

[22] PCT Filed: Mar. 22, 1985

[86] PCT No.: PCT/NL85/00013
  § 371 Date: Nov. 19, 1985
  § 102(e) Date: Nov. 19, 1985

[87] PCT Pub. No.: WO85/04480
  PCT Pub. Date: Oct. 10, 1985

[30] Foreign Application Priority Data

Mar. 22, 1984 [NL] Netherlands ............... 8400916

[51] Int. Cl.[4] .................... G01N 27/00; H01L 29/62; H01L 21/312
[52] U.S. Cl. ........................... 204/416; 437/42; 437/235; 204/418; 357/25
[58] Field of Search .................... 427/82; 437/42, 235; 204/416, 418; 357/25

[56] References Cited

U.S. PATENT DOCUMENTS

| | | | |
|---|---|---|---|
| 3,788,895 | 1/1974 | Schimmer | 427/93 |
| 4,302,530 | 11/1981 | Zemel | 427/82 |
| 4,476,003 | 10/1984 | Frank | 427/82 |

OTHER PUBLICATIONS

Berg et al., "Sensitivity Control of ISFET's by Chemical Surface Modification", *Sensors & Actuators*, vol. 8, (1985), pp. 129–148.

*Primary Examiner*—Michael R. Lusignan
*Assistant Examiner*—Marianne L. Padgett
*Attorney, Agent, or Firm*—Webb, Burden, Robinson & Webb

[57] ABSTRACT

A process for modifying an oxide surface of a semi-conductor material, for example included in an ISFET, wherein a coating of a polymer is applied to the oxide surface. The polymer is chemically bonded to the oxide surface. Optionally a second coating can comprise metal ion complexing groups. The process can be used for manufacturing an ISFET.

25 Claims, 2 Drawing Sheets

METHOD OF PRODUCING AN ISFET AND SAME ISFET

The invention relates to a method of modifying an oxide surface of a semi-conductor material, incorporated for example in an ISFET, in which a polymer coating is applied to the oxide surface.

In analytical chemistry ion sensitive electrodes are used to continuously or otherwise determine positive ions. An important requirement to be met by these electrodes is that they have a long life time and are as chemically inert as possible.

In 1970 Bergveld of the Technical University Twente (TH Twente) described the principle of the so-called "Ion Selective Field Effect Transistor", hereafter referred to as ISFET. The ISFET comprises semi-conductor material, for example p-type silicon, which is provided with an oxide surface, such as $SiO_2$, $Al_2O_3$, $Ta_2O_5$ and $TiO_2$. In the case of a $SiO_2$ oxide surface, for example, the working of this pH sensitive ISFET is based on the fact that Si-OH groups can be protonised and deprotonised respectively, depending on the concentration of protons in the environment surrounding the ISFET. In this way a potential is built up at the $SiO_2$/environment interface, resulting in the occurence of a corresponding charge variance in the silicon. As the potential built up is dependent on the proton concentration in the environment, the proton concentration can be relatively determined in this way.

If the oxide surface is modified as such that another positive ion preferably interacts with the modified oxide surface, an ISFET is made which is suitable for the qualitative and quantitative determination of this other positive ion.

For this purpose, the oxide surface is coated with a layer of a polymer or paste containing suitable (macro) cyclic compounds, which preferably possess a high affinity for a particular metal ion, especially in relation to protons.

By bonding the metal ion in the macrocyclic organic compounds a potential is again created with which the concentrations of this particular positive ion can be determined relatively, and if necessary, in a quantitative manner. The stability of the coating of a polymer applied in this way is, however, not great, because the coating is only physically adhered to the oxide surface, with the result that, in an aqueous environment, water can infiltrate between the coating and the oxide surface, because this oxide surface, in the case of $SiO_2$ for example, has a polarity which more or less corresponds to that of water. In view of the fact that the coating of the polymer is generally apolar, the polymer will detach after the infiltration of water between it and the oxide surface, and the intended selectivity of the ISFET is lost. A second disadvantage is that such a known ISFET often has an excessive pH sensitivity.

Much research has already been directed at modifying for example the $SiO_2$ surface by means of a chemical reaction. A disadvantage of all known techniques is that on the $SiO_2$ surface a number of silanol groups that are present are not always transformed, so that an ISFET manufactured in this way remains pH sensitive.

The British patent application No. 2.017.400 describes the coating of the surface of a gate area of an ISFET with a hydrophobic organic polymer membrane. In this method, prior to the application of the hydrophobic membrane, the oxide surface of the semi-conductor material is treated with a silane coupling agent which couples with the silane groups present on the oxide surface. There is, however, absolutely no question of a chemical bond of the hydrophobic organic polymer membrane subsequently to be applied to the treated oxide surface. On the one hand this is because, according to example 3 of this British publication, the polymer membrane is formed by radical polymerization in the vapour phase, as a result of which the polymer is deposited on the oxide surface of the semi-conductor material physically adheres to it by adsorption. The physically adhered membrane could have been removed, according to the state of the art (Journal Polymer Science, part C, 16, p. 2341, 1967), if washed with a solvent (toluene), which could have removed the physically adhered layer. On the other hand, the life time of the manufactured IGFET is, as stated, only 24 hours. If it had been a case of a chemically bonded polymer membrane, the life time would have been considerably longer, and in an order of magnitude of at least a number of months. From the experimental conditions described (radical polymerization) and the lack of any remark concerning a considerable extension of the life time (a character improvement already long sought after), it can be concluded that the hydrophobic polymer membrane as described in the British patent application 2.017.400 is only physically adhered to the oxide surface of the semi-conductor material.

The invention has for its object the application of a coating on the oxide surface of a semi-conductor material, included for example in an ISFET, as such that this coating is chemically bonded, while such an ISFET is less pH sensitive.

According to the invention this is achieved because the polymer is chemically bonded to the oxide surface.

By coating the oxide surface in this way with an apolar polymer which is chemically bonded to the oxide surface, the silanol groups that have not reacted are generally inaccessible to protons, so that the ISFET becomes less pH sensitive.

There are various methods with which, according to the invention, the polymer, for example a polyvinyl, polyamide, polyurethane or polycarbamate, can be chemically bonded on the oxide surface. Firstly, for example in the case of a vinyl polymer, because the polymer is formed from at least one type of monomers which are polymerized to the oxide surface (in this case the oxide surface acts as initiator of the reaction), secondly in that an alkoxy- and/or halogen vinylsilane, aminosilane, isocyanate silane is reacted with the oxide surface and the silane vinyl, silane epoxy, silane amine groups present on the surface layer are subsequently polymerized with at least one type of vinyl monomers, compounds with more than one alcohol, amine and/or isocyanate group, and thirdly in the case of a vinyl polymer, in that the vinyl polymer is a "living" polymer which is chemically bonded on the oxide surface, whereby it is possible to allow an alkoxy and/or halogen vinyl silane to react with the oxide surface and subsequently to bond the silane vinyl groups present on the surface chemically to the "living" polymer.

It is noted that what is understood by a vinyl polymer is a polymer with a $-(CH_2CHX)_n$ type of chain, where X represents a large number of different substitutes. What is understood by "living" polymers are polymers with a chain end comprising a reactive group which is capable of polymerizing with the same group or with another, for example monomer, group without the addition of an initiator.

According to the invention, the sensitivity of the ISFET to a particular metal ion can be obtained, or alternatively increased, if either the polymer is formed out of a second type of monomers which comprises a metal ion complexing group, or a compound comprising a metal ion complexing group is chemically bonded to the polymer, or a second coating of a polymer comprising metal ion complexing groups is appied to the coating of the polymer chemically bonded on the oxide surface.

In the case where a second coating of a polymer is applied to the first coating which is chemically bonded on the oxide surface, it is possible only to physically adhere the second coating to the first coating, as both coatings possess a generally apolar character, so that, in a polar environment for example, water cannot infiltrate between the two coatings, with the result that, despite the physical adhesion, they continue to show good adhesion in a polar environment. In the case of a physical adhesion, it is possible to adhere the second coating in the form of one or more layers onto the first coating by spinning a solution of polymer comprising metal ion complexing groups.

In the case where the second coating is chemically bonded to the first coating, it is possible to apply the second coating onto the first coating in one or more layers by spinning a solution of monomers comprising metal ion complexing groups, and using an intiator to bond it by polymerization to the remaining vinyl groups present in the first coating.

According to the invention, it is possible that the metal ion complexing group is a crown ether, a cryptand, podand, spherand and/or an ionopher, whereby in the case of a crown ether, for example, 4'-alkyl-benzo-18-crown-6 has been found to be effective.

Another aspect of the invention relates to a process for manufacturing an ISFET, comprising a semi-conductor material having an oxide surface, where a curable resin is applied over the semi-conductor material and through the resin at least one gate is left open right up to the oxide surface. In this known ISFET, in order to prevent the infiltration of water or of another polar fluid between the oxide surface, which possesses a polar character, and the cured resin, which infiltration considerably reduces the life time of the ISFET, it is proposed, in accordance with the invention, that the oxide surface is modified with an apolar chemically bonded polymer prior to the application of the resin, so that infiltration of a polar fluid is in very large measure prevented, because the polarity of the modified surface corresponds generally to that of the cured resin.

Finally the invention relates to an ISFET manufactured according to the invention.

The invention will subsequently be illustrated on the basis of a number of non-limitative embodiments given by way of example.

Many experiments have been performed with p-type silicon plaques of 1×1 cm, obtained by the standard IC-method. At one side of these silicon plaques there is thermally deposited $SiO_2$ with a thickness of ca. 700 Å and on the other side vapour deposited aluminium with a thickness of ca. 5,000 Å.

EXAMPLE I

A plaque of the semi-conductor material to be treated, which had $SiO_2$ as its oxide surface was heated under reflux for 2 hours in a mixture of 0.5 ml mesitylene. The material obtained displayed hydrophobic characteristics. The applied coating of the vinyl polymer, which in this case consisted of polystyrene, had a layer thickness of 200–250 Å (determined using ellipsometry).

EXAMPLE II

On a plaque modified with polystyrene in accordance with example I, a solution of 1% polystyrene (MW 670,000 AE) in toluene was added to the rotary axis at a speed of 3,000 revolutions per minute. After the evaporation of the solvent, the total layer thickness was determined using ellipsometry, and this was found to be 700 Å. This second coating layer of polystyrene is physically adhered to the first chemically bonded polystyrene coating.

Figure 1:
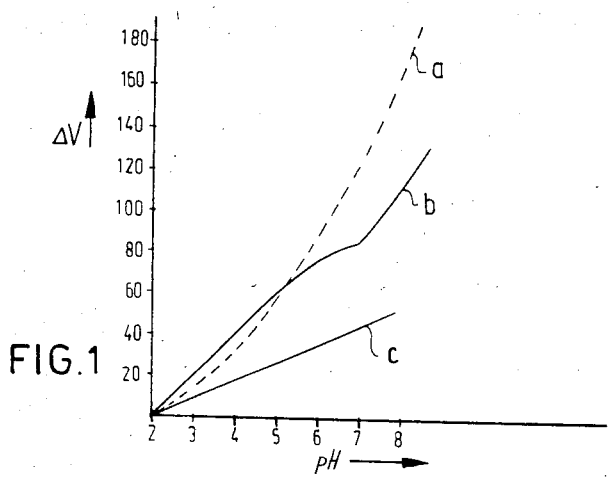
FIG. 1, shows the pH sensitivity of Si plaques where the vertical axis gives the difference in millivolts.

Using the known CV-method, the pH sensitivity of the plaque obtained according to example I and II was subsequently tested. The results are shown in FIG. 1 and compared with a non-treated plaque of silicon. In FIG. 1, the vertical axis gives the voltage difference in millivolts in relation to pH=2, and the horizontal axis gives the pH. The line a relates to a non-treated plaque of silicon and shows clearly a continuous variation in the potential on the oxide surface, particularly in the pH area pH 5–7, so that this untreated plaque of silicon is particularly pH sensitive. The line b relates to a plaque of silicon, of which the oxide surface, according to example I, is provided with a chemically bonded coating of polystyrene with a thickness of 200 Å. In contrast to line a it is clear that the modified plaque of silicon is considerably less pH sensitive, particularly in the pH area pH 5–7. Finally, line c relates to a plaque of silicon manufactured according to example II. Particularly in relation to line b it is clear that, as a result of the application of two coatings, respectively one that is chemically bonded and with a thickness of 200 Å, and one that is physically adhered and with a thickness of 500 Å, this double coating has become particularly impermeable for protons. It is in principle possible to give the first and/or second coating a layered build-up.

ISFETs comprising a plaque of silicon treated according to the invention were measured for different concentrations of K, Li and Cs ions, using 0.15M tetra ethyl ammonium halogenide as reference electrolyte. The measurements are given in the table. pH sensitivity is 23 mV/pH.

TABLE

Voltage difference as a function of K, Li, Cs ion concentration (constant pH 3 or 9) for ISFET according to the invention. Metal complexing group: 4'-alkyl-benzo-18-crown-6.

| Ion | Voltage difference[1],[4] ($\Delta mV/\log M^+$) | | | | |
|---|---|---|---|---|---|
| | I | II | III | IV | V |
| after manufacture[2] | | | | | |
| $K^+$ | 4 | 28 | 34 | 37 | 37 |
| $Li^+$ | 1 | 3 | 7 | 8 | 9 |
| $Cs^+$ | 3 | 17 | 24 | 27 | 28 |

TABLE-continued

Voltage difference as a function of K, Li, Cs ion concentration (constant pH 3 or 9) for ISFET according to the invention. Metal complexing group: 4'-alkyl-benzo-18-crown-6.

| Ion | Voltage difference[1],[4] ($\Delta$mV/log M$^+$) | | | | |
|---|---|---|---|---|---|
| | I | II | III | IV | V |
| after 40 days[2] | | | | | |
| K$^+$ | 4 | 29 | 32 | 39 | 40 |
| Li$^+$ | 1 | 3 | 6 | 5 | 7 |
| after 5 months[3] | | | | | |
| K$^+$ | 2 | 15 | 20 | 28 | 33 |

Figure 3:
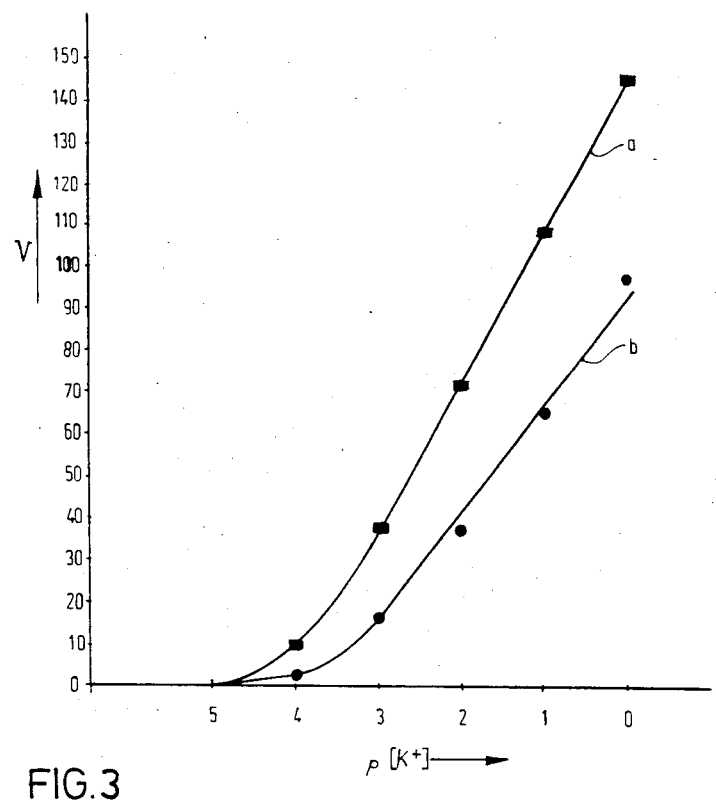
FIG. 3, shows the stability of the ISFET's.

[1] average observations on 8 ISFETs
[2] pH reference electrolyte pH = 9
[3] pH reference electrolyte pH = 3
[4] I: $10^{-5} - 10^{-4}$ M$^+$; II: $10^{-4} - 10^{-3}$ M$^+$; III: $10^{-3} - 10^{-2}$ M$^+$; IV: $10^{-2} - 10^{-1}$ M$^+$; V: $10^{-1} - 0.1$ M$^+$ FIG. 3 shows the stability of the ISFETs. Line a after 3 days with tetra ethyl ammonium bromide (pH=9) as reference electrolyte. Line b after 5 months with tetra ethyl ammonium chloride (pH=3) as reference electrolyte. This change in pH can only result in a small distortion of the measurement results when there are low K+ concentrations because of the competition between K+/H+ on the surface.

EXAMPLE III

1. Polycarbamates

A non-treated plaque silicon was heated for 24 hours at 110° C. in a solution of 3-glycidoxy propyl trimethoxy silane in 2 nl of toluene. The treated plaque was agitated for 4 hours at 50° C. in a solution of a poly- or diamine (for example hexane diamine) in toluene. After washing with toluene, the plaque was placed in a solution of poly- or diisocyanate (for example 4,4'-diphenyl methane diisocyanate (MDI)) in toluene, and agitated for 4 hours at 50° C. This treatment was repeated a number of times, until the desired layer thickness of the polycarbamate was reached.

2. Polyurethanes

A non-treated plaque of silicon was heated for 24 hours at 110° C. in a solution of 0.3 ml trimethoxy amino propyl silane in 2 ml toluene. The treated plaque was subsequently treated with poly- or diisocyanate and then washed with toluene and treated with a polyamine. This treatment was repeated a number of times until the desired layer thickness was reached.

The plaques of silicon provided with a chemically bonded polycarbamate or polyurethane can, in one or a number of treatment steps for the building of the desired layer thickness, additionally and simultaneously be brought into reaction with a ligand having one or a number of isocyanate, amine or alcohol groups. This treatment with the ligand is repeated until the desired degree of saturation of the ligand is reached.

EXAMPLE IV

A non-treated plaque of silicon was heated in a solution of 0.3 ml trichloro vinyl silane in 2 ml toluene successively for 2 hours at 25° C. and 4 hours at a temperature of 90° C. The plaque of silicon was subsequently washed with toluene and diethylether. An alternative was to bring the non-treated plaque of silicon into contact with thrichloro vinyl silane via the vapour phase and to react the plaque with it. For this purpose the non-treated plaque of silicon was placed for 24 hours at 300° C. and 0.2 mmHg in a vessel with a gas communicating connection with another vessel holding trichloro vinyl silane. Hereafter the plaque of silicon, of which the oxide surface was provided with silane vinyl groups, was placed in a solution of 0.6 ml styrene, 106 mg 4'-vinylbenzo(2.2.2)cryptand and 30 mg dibenzoyl peroxide in 2 ml toluene. This solution was subsequently twice degassed at 20 mmHg. and then the reaction vessel was filled with nitrogen. The solution was then heated under nitrogen for 24 hours to a temperature of 90° C. The plaque of silicon was then washed with toluene and diethylether and, using ellipsometry, the layer thickness was determined, and this was found to be 200 to 600 Å.

In a corresponding manner it is possible to use a vinyl monomer containing a crown ether instead of a cryptand.

Figure 2:
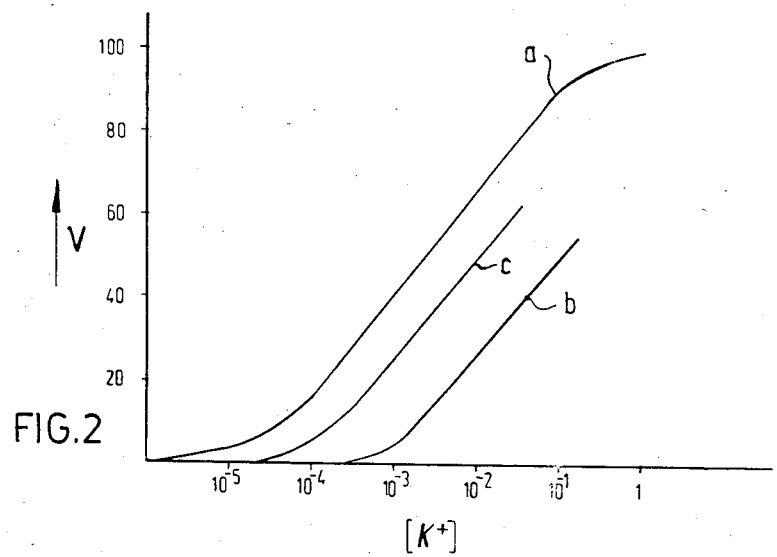
FIG. 2, shows the sensitivity of the modified Si plaques to $K^+$ ions.

FIG. 2 shows the sensitivity of the modified silicon plaques to K+ ions, because the cryptand used (benzo(2.2.2)-cryptand, the line a) and the crown ether (4'-alkyl-benzo-18-crown-6, the lines b and c) have a rather high specific affinity for K+ ions. In similar experimental conditions, such modified silicon plaques were found to possess a relatively very low specific affinity for Li+ ions. Use was made of a KCl solution with as reference electrolyte a 0.1M tetra ethyl ammonium iodide solution. The measurement was again carried out using the known CV-method. The voltage in mvolt in relation to the blank is given along the vertical axis and the K+ concentration in mol/liter along the horizontal axis. For the lines a, b and c in the area form $10^{-4}$ to $10^{-1}$M KCl there is clearly found to be an inherently linear relationship between concentration and voltage, while sensitivity is inherently equal to 25 mV/pK. With respect to the lines b and c it should be mentioned that the line b relates to water used as solvent and the line c to methanol as solvent.

As metal complexing groups cryptands can be considered (see for example Kulstad S. et al Tetrahedron Lett. 21, 643, 1980), as well as crown ethers (Stability and Reactivity of Crown-Ether Complexes, F. de Jong, D. N. Reinhoudt, Academic Press, 1981, London), podands (Vögtle F. et al Angewandte Chemie International Edition English 18, 753, 1979), spherands (Cram, D. J. et al, Journal American Chemical Society 101, 6752, 1979), a variant of spherands, calixa renes (Gutsche C. D. et al, Journal Organic Chemistry 43, 4905, 1978) and ionophors such as Valinomycine (Neupart-Laves, K. et al, Helvetia Chimica Acta, 58, 432, 1975).

EXAMPLE V

"Living" polystyrene and "living" poly-isoprene with an MW of 20,000-30,000 were prepared out of the respective monomers and butyllithium as set out in "Praktikum der makromolekularen organischen Chemie", D. Braun, W. Cherdron, W. Kern, Huethig Verlag, Heidelberg, 1971.

A plaque of silicon was dried under vacuum for 24 hours at 400° C. 10 ml of a "living" polystyrene solution in tetrahydrofuran (ca. 0.05 mol) was then added under extremely dry conditions. After one hour this solution was quenched with 1 ml methanol and the plaque was washed with tetrahydrofuran and diethylether. The thickness of the applied polystyrene layer amounted to 200 Å.

The above reaction was also carried out with a plaque of silicon which was treated for 24 hours at 400° C. with tetrachloro carbon. This reaction also resulted in an applied polystyrene layer with a thickness amounting to 200 Å.

EXAMPLE VI

A plaque modified as in example I was treated for 2 hours at 0° C. under a nitrogen atmosphere and exclusion of moisture with a mixture of 1 g monochloromethyl-methyl ether ($ClCH_2OCH_3$), 0.25 ml tin tetrachloride ($SnCl_4$) and 3 ml carbon disulphide.

After this reaction had ended the solvent was removed and the thus treated plaque was washed successively with 3×10 ml toluene and 2×10 ml ether. Chlorine showed up on the surface under X-ray fluorescence. Ellipsometry showed that the organic surface was intact, and that the layer thickness amounted to 200 Å. The plaque obtained in this manner was subsequently treated for 60 hours at 70° C. with 6 mg sodium hydride and 34 mg 4'-hydroxymethylbenzo-18-crown-6 in 5 ml dry tetrahydrofuran. The plaque was then washed with pure tetrahydrofuran and using a CV measurement the ion sensitivity was shown.

Figure 4:
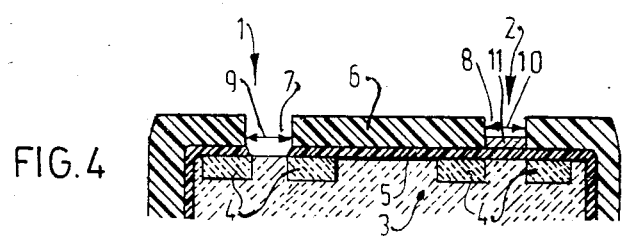
FIG. 4, shows a section through a combination of a pH ISFET (1) and a metallic ion sensitive ISFET (2).

In FIG. 4 a section is given through a combination of a pH ISFET 1 and a metallic ion sensitive ISFET 2 which has, for example, specific affinity for $Ca^{2+}$ ions. Both ISFETs 1, 2 comprise a semi-conductor material 3 of the p-type which includes areas 4 of the n-type. The surface of the semi-conductor material 3 is provided with a coating 5 of an apolar polymer, for example a vinyl polymer, which, according to the invention, is chemically bonded on the oxide surface of the semi-conductor material 3. To the coating 5 that is chemically bonded to the semi-conductor material 3 a cured resin 6, for example Araldite, is applied. Gates 7, 8 in the resin 6 are left open, whereby the part of the coating 5 situated in the area 9 of the gate 7 is removed in a known manner, by etching for example. In this way the gate 7 forms a ion sensitive gate 7.

On the part of the coating 5 situated in the area 10 of the gate 8 a second coating 11 of a polymer comprising crown ether groups is applied, possibly in multiple layers, by spinning, for example. In this way the gate 8 forms a metallic ion sensitive gate 8. Accordingly the specificity for a determined metal ion is determined by the choice of crown ether. Because the coating 5 is chemically bonded to the layer 3 and has an apolar character, which corresponds inherently with the apolar character of the resin 6, infiltration by polar fluid, for example water, between on the one hand the coating 5 and the semi-conductor material 3 and between on the other hand the coating 5 and the resin 6 is thus prevented. In this way the life time of such an ISFET is increased considerably.

Instead of metal ion complexing groups, enzymes can also be bonded covalently on the oxide surface of the semi-conductor material. According to a first embodiment, this can be done be silylating the oxide surface in the previously described ways with a silyl reagent, for example provided with an epoxide group. As a result of the reaction of the enzyme with the epoxide group a structural alteration will occur within the enzyme which results in a decrease of the enzyme activity.

According to a second embodiment, the enzyme can be complexed via its protonised ammonium groups onto for example crown ethers which are, in the previously described manner, chemically bonded in the polymer applied to the oxide surface layer of the semi-conductor material. In this way it is possible to measure enzyme activity in a solution.

We claim:

1. In the process for significantly increasing the useful life of a field effect transistor by on the order of at least one month, which comprises the steps of modifying an oxide surface of said field effect transistor wherein a coating of a polymer is applied to the oxide layer, characterized in that the polymer is chemically bonded to said oxide surface.

2. Process as claimed in claim 1, characterized in that the polymer is formed out of at least one type of monomers which are polymerized to the oxide surface.

3. Process as claimed in claim 1, characterized in that an alkoxy- and/or halogen vinyl silane, epoxysilane, aminosilane, isocyanate silane is reacted with the oxide surface, and that the silane groups present on the surface are subsequently polymerized with at least one type of monomers having a vinyl group or more than one alcohol, amine and/or isocyanate group.

4. Process as claimed in claim 1, characterized in that the polymer is a "living" polymer which is chemically bonded to the oxide surface.

5. Process as claimed in claim 4, characterized in that on alkoxy- and/or halogen vinyl silane is reacted with the oxide surface and that the silane vinyl groups present on the surface are subsequently bonded chemically to the "living" polymer.

6. Process as claimed in claim 1, characterized in that the polymer is polyurethane, polyamide and/or polycarbonate.

7. Process as claimed in any of the claims 2-6, characterized in that the polymer is formed with the inclusion of a second type of monomers which comprise a metal ion complexing group.

8. Process as claimed in any of the claims 2-6, characterized in that a compound comprising a metal ion complexing group is chemically bonded to the polymer.

9. Process as claimed in claim 7, characterized in that the metal ion complexing group is a crown ether, cryptand, podand, spherand and/or ionophor.

10. Process as claimed in claim 9, characterized in that the crown ether is 4'-alkyl-benzo-18-crown-6.

11. Process as claimed in claim 1, characterized in that a second coating of a polymer comprising a metal ion complexing group is applied to the coating of the vinyl chemically bonded to the oxide surface.

12. Process as claimed in claim 11, characterized in that the second coating is physically adhered to the first coating.

13. Process as claimed in claim 12, characterized in that the second coating, in the form of one or more layers, is adhered to the first coating by spinning of a solution of the polymer comprising metal ion complexing groups.

14. Process as claimed in claim 11, characterized in that the second coating is chemically bonded to the first coating.

15. Process as claimed in claim 14, characterized in that the second coating, in one or more layers is applied to the first coating, by spinning of a solution of vinyl monomers comprising metal ion complexing groups, and in using an initiator is bonded to remaining vinyl groups present in the first coating.

16. Process as claimed in claim 11, characterized in that the metal ion complexing group is a crown ether, cryptand, podand, spherand and/or ionophor.

17. Process as claimed in claim 16, characterized in that the crown ether group is 4'-alkyl-benzo-18-crown-6.

18. Process for manufacturing an ISFET, comprising a semi-conductor material having an oxide surface, whereby a curable resin is applied over the semi-conductor material, and through the resin up to the oxide surface at least one gate is left, characterized in that prior to the application of the resin, the oxide surface is modified with a polymer as claimed in any of the claims 1-6, and that optionally at the location of the gate, the polymer is removed.

19. ISFET provided with a semi-conductor material having an oxide surface, characterized by at least one polymer chemically bonded on the oxide surface, as claimed in any of the claims 1-6.

20. In the method of making a field effect transistor having an insulated gate region, the steps of providing a semiconductor body having p- and n-regions defining a surface including the insulated gate region, and significantly increasing the useful life of the transistor, while it is in contact with an environment having polarity of one kind, by chemically bonding a first polymer having polarity opposite that of said one kind to said surface.

21. In the method as defined in claim 20 wherein the useful life of the transistor while it is in contact with the environment is at least a number of months.

22. In the method of significantly increasing the useful life of a field effect transistor, having a sensitive gate region, when such field effect transistor is in contact with a polar liquid being monitored for the presence of an entity in the liquid to which the gate region is sensitive, which comprises the steps of providing a semiconductor body having an oxide layer of polar character on a surface thereof which encompasses and defines the sensitive gate region of the field effect transistor, and chemically bonding a layer of a first polymer having an apolar character on the oxide layer of the semiconductor body.

23. In the method as defined in claim 22 including the step of coating the first polymer layer with a layer of a second polymer having an apolar character and exposing a selected area of the first polymer layer overlying the sensitive gate region through the second polymer layer.

24. In the method as defined in claim 23 including the step of removing the selected area of the first polymer layer to expose the oxide layer therebeneath.

25. In the method as defined in claim 24 including the step of coating the selected area of the exposed first polymer layer with a further layer of a polymer having a sensitivity to a selected metallic ion, the thicknesses of the layer of the first polymer and the further layer of polymer having sensitivity to the selected metallic ion being sufficient to render the gate region substantially insensitive to hydrogen ions.

* * * * *

UNITED STATES PATENT AND TRADEMARK OFFICE
CERTIFICATE OF CORRECTION

PATENT NO. : 4,735,702

DATED : April 5, 1988

INVENTOR(S) : David N. Reinhoudt, Marcel L. M. Pennings and Auke G. Talma

It is certified that error appears in the above-identified patent and that said Letters Patent is hereby corrected as shown below:

Column 6 Line 28 "form" should read --from--.

Column 7 Line 35 "a" should read --an--.

Column 8 Line 28 "polycarbonate" should read --polycarbamate--.

Signed and Sealed this

Twenty-fourth Day of January, 1989

*Attest:*

DONALD J. QUIGG

*Attesting Officer*   *Commissioner of Patents and Trademarks*